US00PP29145P3

(12) United States Plant Patent
Park

(10) Patent No.: US PP29,145 P3
(45) Date of Patent: Mar. 20, 2018

(54) ***COREOPSIS* PLANT NAMED 'URIBL02'**

(50) Latin Name: ***Coreopsis rosea*×*Coreopsis verticillata***
Varietal Denomination: URIBL02

(71) Applicant: Uriseed Institute, Icheon-si (KR)

(72) Inventor: Kong Young Park, Icheon-si (KR)

(73) Assignee: URISEED INSTITUTE, Icheon-si (KR)

( * ) Notice: Subject to any disclaimer, the term of this patent is extended or adjusted under 35 U.S.C. 154(b) by 0 days.

(21) Appl. No.: 14/999,137

(22) Filed: Mar. 31, 2016

(65) Prior Publication Data

US 2017/0049031 P1 Feb. 16, 2017

(30) Foreign Application Priority Data

Aug. 14, 2015 (EM) ..... 20151904

(51) Int. Cl.
*A01H 5/02* (2006.01)

(52) U.S. Cl.
USPC ..... Plt./417

(58) Field of Classification Search
USPC ..... Plt./417
CPC ..... A01H 5/025; A01H 5/02; A01H 5/00
See application file for complete search history.

(56) References Cited

U.S. PATENT DOCUMENTS

PP15,455 P3 * 12/2004 Faria ..... Plt./417

OTHER PUBLICATIONS

Jala Morphological Change Due to Effects of Acute Gamma Ray on Wishbone Flower (*Torenia fourmieri*) in Vitro, 2011 International Transaction Journal of Engineering, Management, & Applied Sciences & Technologies, vol. 2 No. 4, 375-383.*
Park et al. Development of a New *Coreopsis* Variety 'Uridream Pink' by Gamma-ray Irradiation, Kor. J. Hort. Sci. Technol. 32(6):906-911, 2014.*
English translation of Park et al. 2017, 16 pp.*

* cited by examiner

*Primary Examiner* — June Hwu
(74) *Attorney, Agent, or Firm* — Penny J. Aguirre

(57) ABSTRACT

A new cultivar of hybrid *Coreopsis* plant named 'URIBLO2', that is characterized by its dwarf plant habit, by its large inflorescences, its ray florets ray florets that are light red-purple in color with a yellow base, and its disk florets that are orange-red in color.

2 Drawing Sheets

Botanical Classification: *Coreopsis rosea x Coreopsis verticillata.*

Variety Denomination: 'URIBLO2'.

CROSS REFERENCE TO RELATED APPLICATIONS

This application is co-pending with U.S. Plant Patent Applications filed for plants derived from the same breeding programs that is entitled *Coreopsis* Plant Named 'URIBLO1' (U.S. Plant patent application Ser. No. 14/999,120).

BACKGROUND OF THE INVENTION

The present invention relates to a new and distinct cultivar of *Coreopsis* plant, botanically of hybrid origin and known as *Coreopsis* 'URIBLO2' referred to hereinafter by its cultivar name, 'URIBLO2'. The new cultivar of *Coreopsis* is an herbaceous perennial grown for landscape and container use.

The new invention arose from an ongoing controlled breeding program in Icheon-si, Korea. The objective of the breeding program is to develop hybrid cultivars of *Coreopsis* with unique flower colors and dwarf plant habit.

The new cultivar arose as a mutation using gamma radiation of rooted cuttings of unknown, unnamed proprietary plants from the inventor's breeding program in January of 2010. 'Limerock Ruby' (U.S. Plant Patent No. 15,455) and addition cultivars were initially used in the breeding program in prior years to obtain initial primary mutations and subsequent rounds of gamma radiation were performed on proprietary seedlings until 'URIBLO2' was selected in September 2010 as a single unique plant amongst the resulting seedlings.

Asexual propagation of the new cultivar was first accomplished by stem cuttings under the direction of the inventor in Icheon-si, Korea in September of 2010. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'URIBLO2' as unique cultivar of *Coreopsis*.

1. 'URIBLO2' exhibits a dwarf plant habit.
2. 'URIBLO2' exhibits large inflorescences.

3. 'URIBLO2' exhibits ray florets that are light red-purple in color with a yellow base.
4. 'URIBLO2' exhibits disk florets that are orange-red in color.

'URIBLO2' can be most closely compared to 'URIBLO1', 'Limerock Ruby' and 'Uridream Pink' (not patented). 'URIBLO1' is similar to 'URIBLO2' in having a dwarf plant habit. 'URIBLO1' differs from 'URIBLO2' in having any ray florets that are crimson red in color, in having a slightly smaller plant size, and in having inflorescences that are slightly smaller in size. 'Limerock Ruby', differs from 'URIBLO2' in having a taller plant height and wider plant spread, in having inflorescences that are smaller in size with ray florets that are smaller in size. 'Uridream Pink' differs from 'URIBLO2' in having a taller plant height, longer internode lengths, smaller inflorescences, and ray florets that are much darker pink in color.

BRIEF DESCRIPTION OF THE DRAWINGS

The accompanying colored photographs illustrate the overall appearance and distinct characteristics of the new *Coreopsis*. The photographs were taken of a 3 month-old plant of 'URIBLO2' as grown outdoors in BosKoop, The Netherlands.

The photograph in FIG. 1 provides a side view of a plant of 'URIBLO2' in bloom.

Figure 1:
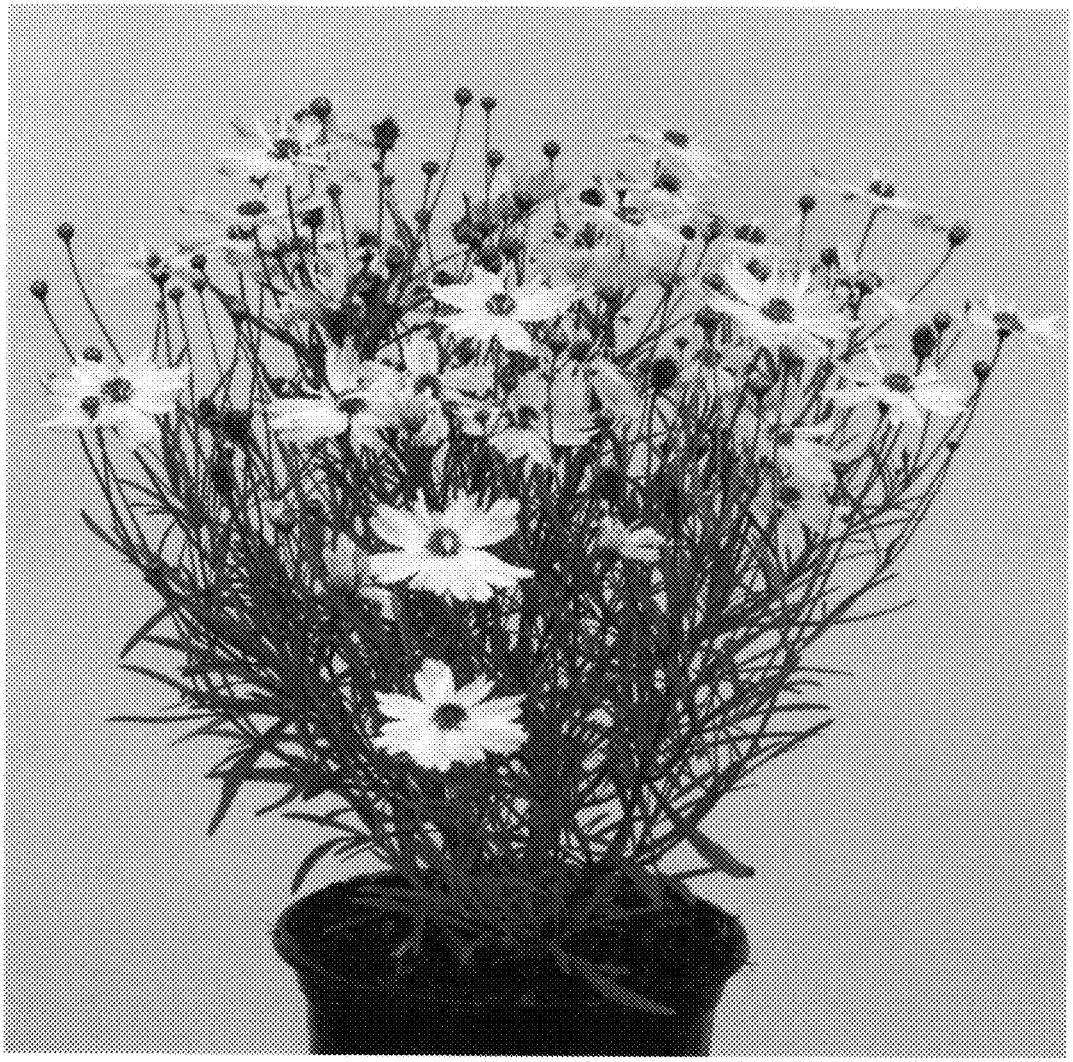
Figure 2:
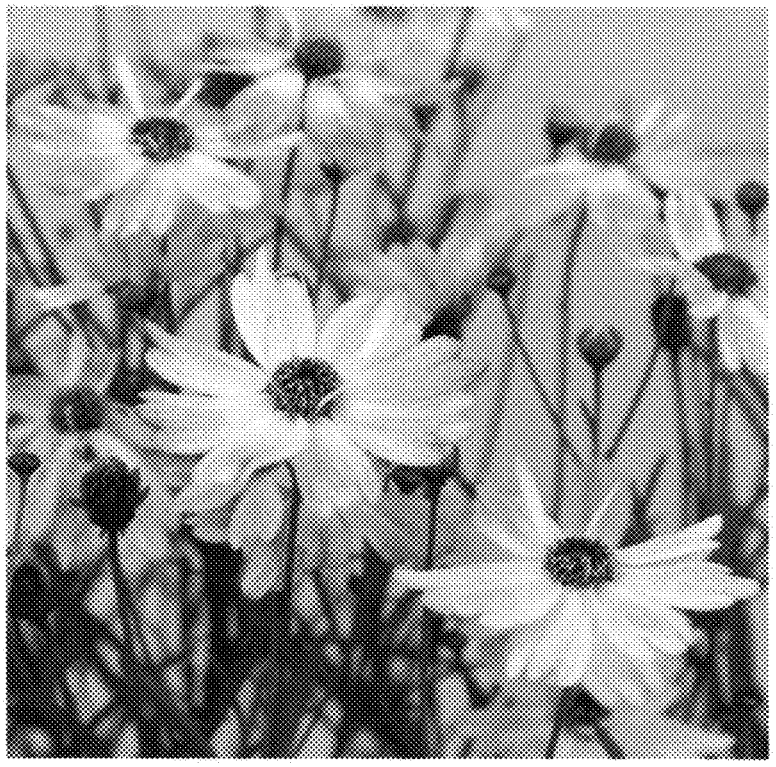

The photograph in FIG. 2 provides a close-up view of the inflorescences of 'URIBLO2'.

Figure 3:
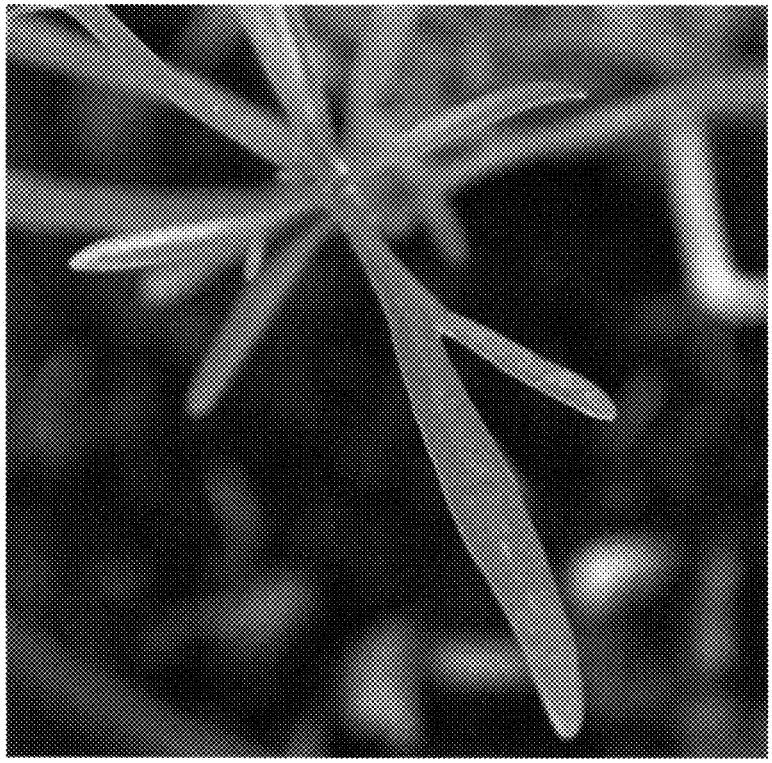

The photograph in FIG. 3 provides a close-up view of the foliage of 'URIBLO2'.

The colors in the photograph are as close as possible with the photographic and printing technology utilized and the color values cited in the Detailed Botanical Description accurately describe the colors of the new *Coreopsis*.

DETAILED BOTANICAL DESCRIPTION

The following is a detailed description of 3 month-old plants of the new cultivar as grown outdoors in 13-cm containers Boskoop, The Netherlands. The phenotype of the new cultivar may vary with variations in environmental, climatic, and cultural conditions, as it has not been tested under all possible environmental conditions. The color determination is in accordance with the 2007 RHS Colour Chart of the Royal Horticultural Society, London, England, except where general color terms of ordinary dictionary significance are used.

General Description:

Blooming period.—Early summer to late summer in The Netherlands.

Plant type.—Herbaceous perennial.

Plant habit.—Dwarf and upright.

Height and spread.—An average of 23.7 cm in height and 26.4 cm in width.

Cold hardiness.—At least to U.S.D.A Zone 4.

Diseases and Pests.—No susceptibility or resistance to diseases or pests has been observed.

Root description.—Fibrous when young, becoming fleshy with age, 162D in color.

Propagation.—Stem cuttings.

Root development.—An average of 10 days for root initiation and about 5 weeks to produce a young rooted plant in a 10-cm container.

Growth rate.—Moderate.

Stem Description:

Shape.—Oval and slightly ridged.

Stem color.—143B.

Stem size.—An average of 7.3 cm in length (excluding inflorescence) and 1.5 mm in diameter.

Stem surface.—Glabrous, glossy, slightly axially ribbed.

Stem aspect.—Upward and outward.

Stem strength.—Strong.

Branching habit.—Well-branched, an average of 38 lateral branches.

Internode length.—An average of 2.4 cm.

Foliage Description:

Leaf type.—Single.

Leaf division.—Simple.

Leaf margins.—Entire to two-lobed.

Leaf size.—Variable; up to 4.3 cm in length and 1.7 cm in width when entire and up to 5.4 cm in length and 4 mm in width when two-lobed.

Leaf shape.—Narrow lariceolate.

Leaf base.—Narrow curieate

Leaf apex.—Acute.

Leaf venation.—Pinnate, color; upper surface 137B and lower surface 144A.

Leaf attachment.—Sessile.

Leaf arrangement.—Opposite.

Leaf surface.—Both surfaces dull and glabrous.

Leaf color.—Young and mature upper surface; 137B and young and mature lower surface; 143A.

Leaf number.—An average of 8 leaves (4 pairs) per stem.

Inflorescence Description:

Inflorescence type.—Terminal capitulate, with a single row of ray florets surrounding disk florets in the center.

Lastingness of inflorescence.—An average of 3 weeks, self-cleaning.

Fragrance.—Faint, of musk and straw.

Quantity of inflorescence size.—An average of 1 per lateral branch.

Inflorescence size.—An average of 4.0 cm in diameter and 1.2 cm in height, disk portion an average of 7 mm in diameter.

Inflorescence buds.—An average of 5 mm in depth and in diameter, globular in shape, color; 147C with apex, 168B to 168C.

Peduncle.—Primary; on average of 7.4 cm in length and 1 mm in width, held straight upright, secondary; an average of 5.2 cm in length and 1 mm in width, held at an average angle of 30° to primary peduncle, slightly glossy and glabrous on all surfaces and 143B in color.

Involucral bracts:

Bract number.—Two rows of 8.

Bract arrangement.—Rotate.

Bract size.—Outer bracts; an average of 3 mm in length and 2 mm in width, inner bracts; an average of 7 mm in length and 4 mm in width.

Bract color.—Inner bracts; 24A with base 146A and outer bracts; 143A.

Bract texture.—Glabrous and slightly glossy on outer and inner surfaces of outer and inner bracts.

Bract apex.—Acute on outer and inner bracts.

Bract base.—Broadly cuneate on outer and inner bracts.

Bract margins.—Entire.

Bract shape.—Outer bracts; narrow ovate, inner bracts; ovate.

Ray Florets (sterile):

Number.—An average of 8 arranged primarily in one row,

Shape.—Obovate.
Size.—An average of 1.8 cm in length and 9 mm in width.
Apex.—Irregularly lobed with an average of 3 acute lobes, center lobe is about 2 mm longer than the lateral lobes.
Base.—Rounded.
Margins.—Entire with apex lobed.
Aspect.—Held horizontal.
Texture.—Both surfaces; glabrous and dull, upper surface very slightly velvety and lower surface moderately carinate.
Color.—Upper surface when opening; 70B to 70C with base 3C to 3D, lower surface when opening; 73D with apex 75A to 75B and base 2D, upper surface when fully open; 75B to 75C marbled 76C to 76D with base 2D, lower surface when fully open; 158D suffused with 75D base 2D, color not fading.
Petaloids.—Ray floret like; average of 4 per inflorescence, an average of 5 mm in length and 2 mm in width, narrow obovate to linear in shape, rounded to acute apex, cuneate base, coloration matches ray floret color.
Disk florets (perfect):
Shape.—Tubular, spirally arranged on disc.
Apex.—Acute.
Base.—Lower 87.5% fused into tube.
Number.—About 80.
Size.—An average of 4.5 mm in length and 1.0 mm in width at the apex and 0.4 mm in width at the base.
Color.—En masse; a mix of 15B to 15C and 179A, corolla; base of tube is 15B to 15C in color, flared portion is 179A.
Texture.—Both surfaces; glabrous and dull.
Receptacle.—An average of 1.5 mm in diameter and 1 mm in depth, 143B in color.
Reproductive Organs:
Presence.—Disk florets are perfect, ray florets are sterile.
Gynoecium.—Pistil; 1, an average of 3 mm in length, style; an average of 2.5 mm in length and 16A in color, stigma; decurrent and 23A in color, ovary is 151C in color.
Androecium.—Stamens; 5, anther; basiFixed and linear in shape, an average of 1.5 mm in length and 203D in color, pollen; moderate in quantity and 17B in color.
Fruit/seed.—No fruit or seed development was observed.

It is claimed:

1. A new and distinct cultivar of *Coreopsis* plant named 'URIBLO2' as herein illustrated and described.

* * * * *